(12) United States Patent
Feeser

(10) Patent No.: US 8,025,692 B2
(45) Date of Patent: Sep. 27, 2011

(54) STENT DELIVERY SYSTEM

(75) Inventor: Jörg Feeser, Königsbach-Stein (DE)

(73) Assignee: Angiomed GmbH & Co. Medizintechnik KG, Karlsruhe (DE)

( * ) Notice: Subject to any disclaimer, the term of this patent is extended or adjusted under 35 U.S.C. 154(b) by 1960 days.

(21) Appl. No.: 10/490,752

(22) PCT Filed: Oct. 2, 2002

(86) PCT No.: PCT/EP02/11082
§ 371 (c)(1),
(2), (4) Date: Jul. 12, 2004

(87) PCT Pub. No.: WO03/030783
PCT Pub. Date: Apr. 17, 2003

(65) Prior Publication Data
US 2005/0038493 A1  Feb. 17, 2005

(30) Foreign Application Priority Data
Oct. 2, 2001 (GB) .................................. 0123633.0

(51) Int. Cl.
*A61F 2/06* (2006.01)
(52) U.S. Cl. ..................... 623/1.12; 606/108; 604/264
(58) Field of Classification Search .............. 606/108, 606/191, 198, 194, 195, 200; 623/1.12; 604/264, 604/523, 524, 525
See application file for complete search history.

(56) References Cited

U.S. PATENT DOCUMENTS

| 3,485,234 A | 12/1969 | Stevens |
| 4,580,568 A | 4/1986 | Gianturco |
| 4,636,346 A | 1/1987 | Gold et al. |
| 4,759,748 A | 7/1988 | Reed |
| 4,768,507 A | 9/1988 | Fischell et al. |
| 4,817,613 A | 4/1989 | Jaraczewski et al. |
| 4,842,590 A | 6/1989 | Tanabe et al. |
| 4,950,227 A | 8/1990 | Savin et al. |
| 4,979,280 A | 12/1990 | Weil |
| 5,026,377 A | 6/1991 | Burton et al. |

(Continued)

FOREIGN PATENT DOCUMENTS

CA    2449961 A1    1/2003

(Continued)

OTHER PUBLICATIONS

Feb. 4, 2008 International Search Report in international application No. PCT/EP2007/063347 filed on Dec. 5, 2007.

(Continued)

*Primary Examiner* — Anhtuan Nguyen
*Assistant Examiner* — Julie A Szpira
(74) *Attorney, Agent, or Firm* — Rutan & Tucker, LLP

(57) ABSTRACT

A stent delivery catheter for rapid exchange carries at its distal end a sleeve (12) to surround a self-expanding stent (10) and a tension wire (30) running the length of the catheter to release the stent by proximal withdrawal of the sleeve. A tubular catheter shaft (62) surrounds the tension wire. An inner catheter (44) defines a guidewire lumen (48) with a proximal guidewire exit part (58) at the distal end of the catheter shaft. The inner catheter carries an abutment (32) to restrain the stent from moving proximally when the sleeve is pulled proximally. There is a gap (74) between the abluminal surface of the inner catheter and the luminal surface of the catheter shaft, in which the tension wire is accommodated.

20 Claims, 4 Drawing Sheets

U.S. PATENT DOCUMENTS

| | | | |
|---|---|---|---|
| 5,061,257 A | 10/1991 | Martinez et al. | |
| 5,085,662 A | 2/1992 | Willard | |
| 5,158,548 A | 10/1992 | Lau et al. | |
| 5,201,757 A | 4/1993 | Heyn et al. | |
| 5,221,372 A | 6/1993 | Olson | |
| 5,234,416 A | 8/1993 | Macaulay et al. | |
| 5,254,107 A | 10/1993 | Soltesz | |
| 5,275,152 A | 1/1994 | Krauter et al. | |
| 5,290,295 A | 3/1994 | Querals et al. | |
| 5,443,477 A | 8/1995 | Marin et al. | |
| 5,445,646 A | 8/1995 | Euteneuer et al. | |
| 5,453,090 A | 9/1995 | Martinez et al. | |
| 5,484,444 A | 1/1996 | Braunschweiler et al. | |
| 5,507,768 A | 4/1996 | Lau et al. | |
| 5,507,769 A | 4/1996 | Marin et al. | |
| 5,522,883 A | 6/1996 | Slater et al. | |
| 5,534,007 A * | 7/1996 | St. Germain et al. | 623/1.11 |
| 5,571,135 A | 11/1996 | Fraser et al. | |
| 5,571,168 A | 11/1996 | Toro | |
| 5,603,698 A | 2/1997 | Roberts et al. | |
| 5,603,705 A | 2/1997 | Berg | |
| 5,617,900 A | 4/1997 | Weil | |
| 5,618,300 A | 4/1997 | Marin et al. | |
| 5,634,928 A | 6/1997 | Fischell et al. | |
| 5,643,278 A | 7/1997 | Wijay | |
| 5,662,622 A | 9/1997 | Gore et al. | |
| 5,662,703 A | 9/1997 | Yurek et al. | |
| 5,674,208 A | 10/1997 | Berg et al. | |
| 5,683,451 A | 11/1997 | Lenker et al. | |
| 5,690,642 A | 11/1997 | Osborne et al. | |
| 5,690,644 A | 11/1997 | Yurek et al. | |
| 5,700,269 A | 12/1997 | Pinchuk et al. | |
| 5,702,418 A | 12/1997 | Ravenscroft | |
| 5,707,376 A | 1/1998 | Kavteladze et al. | |
| 5,709,703 A | 1/1998 | Lukic et al. | |
| 5,733,267 A | 3/1998 | Del Toro | |
| 5,738,667 A | 4/1998 | Solar | |
| 5,741,327 A | 4/1998 | Frantzen | |
| 5,772,668 A | 6/1998 | Summers et al. | |
| 5,772,669 A | 6/1998 | Vrba | |
| 5,788,707 A | 8/1998 | Del Toro et al. | |
| 5,792,144 A * | 8/1998 | Fischell et al. | 606/108 |
| 5,792,365 A | 8/1998 | Torini et al. | |
| 5,797,952 A * | 8/1998 | Klein | 623/1.12 |
| 5,811,043 A | 9/1998 | Horrigan et al. | |
| 5,817,101 A | 10/1998 | Fiedler | |
| 5,824,041 A | 10/1998 | Lenker et al. | |
| 5,910,145 A * | 6/1999 | Fischell et al. | 606/108 |
| 5,951,495 A | 9/1999 | Berg et al. | |
| 5,954,651 A | 9/1999 | Berg et al. | |
| 5,957,930 A | 9/1999 | Vrba | |
| 5,968,052 A | 10/1999 | Sullivan, III et al. | |
| 5,980,533 A | 11/1999 | Holman | |
| 5,984,964 A | 11/1999 | Roberts et al. | |
| 5,993,460 A | 11/1999 | Beitelia et al. | |
| 6,019,778 A | 2/2000 | Wilson et al. | |
| 6,039,749 A | 3/2000 | Marin et al. | |
| 6,042,588 A | 3/2000 | Munsinger et al. | |
| 6,042,589 A | 3/2000 | Marianne | |
| 6,077,295 A | 6/2000 | Limon et al. | |
| 6,080,102 A | 6/2000 | Konou et al. | |
| 6,096,045 A | 8/2000 | Del Toro et al. | |
| 6,126,685 A | 10/2000 | Lenker et al. | |
| 6,143,016 A | 11/2000 | Bleam et al. | |
| 6,146,415 A | 11/2000 | Fitz | |
| 6,152,944 A | 11/2000 | Holman et al. | |
| 6,168,610 B1 | 1/2001 | Marin et al. | |
| 6,168,616 B1 | 1/2001 | Brown, III | |
| 6,177,140 B1 | 1/2001 | Patil et al. | |
| 6,190,393 B1 | 2/2001 | Bevier et al. | |
| 6,206,888 B1 | 3/2001 | Bicek et al. | |
| 6,212,422 B1 | 4/2001 | Berg et al. | |
| 6,217,586 B1 | 4/2001 | Mackenzie | |
| 6,221,081 B1 | 4/2001 | Mikus et al. | |
| 6,228,110 B1 | 5/2001 | Munsinger | |
| 6,238,402 B1 | 5/2001 | Sullivan, III et al. | |
| 6,238,410 B1 | 5/2001 | Vrba et al. | |
| 6,238,430 B1 | 5/2001 | Klumb et al. | |
| 6,241,758 B1 | 6/2001 | Cox | |
| 6,254,608 B1 | 7/2001 | Solar | |
| 6,254,609 B1 | 7/2001 | Vrba et al. | |
| 6,254,611 B1 | 7/2001 | Vrba | |
| 6,264,671 B1 | 7/2001 | Stack et al. | |
| 6,293,966 B1 | 9/2001 | Frantzen | |
| 6,296,622 B1 | 10/2001 | Kurz et al. | |
| 6,306,145 B1 | 10/2001 | Leschinsky | |
| 6,331,186 B1 | 12/2001 | Wang et al. | |
| 6,342,066 B1 * | 1/2002 | Toro et al. | 623/1.11 |
| 6,350,278 B1 | 2/2002 | Lenker et al. | |
| 6,352,553 B1 | 3/2002 | van der Burg et al. | |
| 6,352,561 B1 | 3/2002 | Leopold et al. | |
| 6,355,060 B1 | 3/2002 | Lenker et al. | |
| 6,361,555 B1 | 3/2002 | Wilson | |
| 6,368,344 B1 | 4/2002 | Fitz | |
| 6,371,979 B1 | 4/2002 | Beyar et al. | |
| 6,375,676 B1 | 4/2002 | Cox | |
| 6,379,365 B1 * | 4/2002 | Diaz | 606/108 |
| 6,380,457 B1 | 4/2002 | Yurek et al. | |
| 6,387,118 B1 | 5/2002 | Hanson | |
| 6,391,050 B1 | 5/2002 | Broome | |
| 6,391,051 B2 | 5/2002 | Sullivan, III et al. | |
| 6,402,760 B1 | 6/2002 | Fedida | |
| 6,413,269 B1 | 7/2002 | Bui et al. | |
| 6,425,898 B1 | 7/2002 | Wilson et al. | |
| 6,432,129 B2 | 8/2002 | DiCaprio | |
| 6,443,979 B1 | 9/2002 | Stalker et al. | |
| 6,468,298 B1 | 10/2002 | Pelton | |
| 6,482,211 B1 | 11/2002 | Choi | |
| 6,488,694 B1 | 12/2002 | Lau et al. | |
| 6,505,066 B2 | 1/2003 | Berg et al. | |
| 6,514,196 B1 | 2/2003 | Sullivan et al. | |
| 6,514,280 B1 | 2/2003 | Gilson | |
| 6,517,547 B1 | 2/2003 | Feeser et al. | |
| 6,517,569 B2 | 2/2003 | Mikus et al. | |
| 6,520,983 B1 | 2/2003 | Colgan et al. | |
| 6,530,947 B1 | 3/2003 | Euteneuer et al. | |
| 6,554,841 B1 | 4/2003 | Yang | |
| 6,572,643 B1 | 6/2003 | Gharibadeh | |
| 6,576,002 B2 | 6/2003 | Dobak, III | |
| 6,579,297 B2 | 6/2003 | Bicek et al. | |
| 6,582,460 B1 | 6/2003 | Cryer | |
| 6,592,569 B2 | 7/2003 | Bigus et al. | |
| 6,599,296 B1 | 7/2003 | Gillick et al. | |
| 6,605,109 B2 | 8/2003 | Fiedler | |
| 6,613,075 B1 | 9/2003 | Healy et al. | |
| 6,626,934 B2 | 9/2003 | Blaeser et al. | |
| 6,629,981 B2 | 10/2003 | Bui et al. | |
| 6,629,992 B2 | 10/2003 | Bigus et al. | |
| 6,641,606 B2 | 11/2003 | Ouriel et al. | |
| 6,656,212 B2 | 12/2003 | Ravenscroft et al. | |
| 6,656,213 B2 | 12/2003 | Solem | |
| 6,660,031 B2 | 12/2003 | Tran et al. | |
| 6,663,614 B1 | 12/2003 | Carter | |
| 6,663,666 B1 | 12/2003 | Quiachon et al. | |
| 6,676,666 B2 | 1/2004 | Vrba et al. | |
| 6,676,693 B1 | 1/2004 | Belding et al. | |
| 6,689,120 B1 | 2/2004 | Gerdts | |
| 6,695,812 B2 * | 2/2004 | Estrada et al. | 604/103.09 |
| 6,695,862 B2 | 2/2004 | Cox et al. | |
| 6,699,274 B2 | 3/2004 | Stinson | |
| 6,702,843 B1 | 3/2004 | Brown et al. | |
| 6,726,712 B1 | 4/2004 | Raeder-Devens et al. | |
| 6,726,714 B2 | 4/2004 | DiCaprio et al. | |
| 6,736,839 B2 | 5/2004 | Cummings | |
| 6,743,219 B1 | 6/2004 | Dwyer et al. | |
| 6,749,627 B2 | 6/2004 | Thompson et al. | |
| 6,773,446 B1 | 8/2004 | Dwyer et al. | |
| 6,780,199 B2 | 8/2004 | Solar et al. | |
| 6,786,918 B1 | 9/2004 | Krivoruchko et al. | |
| 6,790,221 B2 | 9/2004 | Monroe et al. | |
| 6,827,731 B2 | 12/2004 | Armstrong et al. | |
| 6,830,575 B2 | 12/2004 | Stenzel et al. | |
| 6,843,802 B1 | 1/2005 | Villalobos et al. | |
| 6,849,084 B2 | 2/2005 | Rabkin et al. | |
| 6,858,034 B1 | 2/2005 | Hijlkema et al. | |
| 6,860,898 B2 | 3/2005 | Stack et al. | |
| 6,866,669 B2 | 3/2005 | Buzzard et al. | |

| | | |
|---|---|---|
| 6,884,259 B2 | 4/2005 | Tran et al. |
| 6,899,727 B2 | 5/2005 | Armstrong et al. |
| 6,926,732 B2 | 8/2005 | Derus et al. |
| 6,939,352 B2 | 9/2005 | Buzzard et al. |
| 6,942,688 B2 | 9/2005 | Bartholf et al. |
| 6,945,989 B1 | 9/2005 | Betelia et al. |
| 7,001,423 B2 | 2/2006 | Euteneuer et al. |
| 7,025,773 B2 | 4/2006 | Gittings et al. |
| 7,052,511 B2 | 5/2006 | Weldon et al. |
| 7,074,236 B2 | 7/2006 | Rabkin et al. |
| 7,147,657 B2 | 12/2006 | Chiang et al. |
| 7,163,552 B2 | 1/2007 | Diaz |
| 7,172,617 B2 | 2/2007 | Colgan et al. |
| 7,198,636 B2 | 4/2007 | Cully et al. |
| 7,297,302 B2 | 11/2007 | Berg et al. |
| 7,550,001 B2 | 6/2009 | Dorn et al. |
| 2001/0034549 A1 | 10/2001 | Bartholf et al. |
| 2002/0016597 A1 | 2/2002 | Dwyer et al. |
| 2002/0077691 A1 | 6/2002 | Nachtigall |
| 2002/0183826 A1 | 12/2002 | Dorn et al. |
| 2003/0050686 A1 | 3/2003 | Raeder-Devens et al. |
| 2003/0109886 A1 | 6/2003 | Keegan et al. |
| 2004/0006380 A1 | 1/2004 | Buck et al. |
| 2004/0015228 A1 | 1/2004 | Lombardi et al. |
| 2004/0073291 A1 | 4/2004 | Brown et al. |
| 2004/0127912 A1 | 7/2004 | Rabkin et al. |
| 2004/0148009 A1 | 7/2004 | Buzzard et al. |
| 2004/0153137 A1 | 8/2004 | Gaschino et al. |
| 2004/0181239 A1 | 9/2004 | Dorn et al. |
| 2004/0186547 A1 | 9/2004 | Dorn et al. |
| 2004/0193180 A1 | 9/2004 | Buzzard et al. |
| 2004/0199240 A1 | 10/2004 | Dorn |
| 2004/0215229 A1 | 10/2004 | Coyle |
| 2004/0215317 A1 | 10/2004 | Cummings |
| 2004/0254637 A1 | 12/2004 | Yang et al. |
| 2005/0004515 A1 | 1/2005 | Hart et al. |
| 2005/0021123 A1 | 1/2005 | Dorn et al. |
| 2005/0027345 A1 | 2/2005 | Horan et al. |
| 2005/0065590 A1 | 3/2005 | Shelso |
| 2005/0065591 A1 | 3/2005 | Moberg et al. |
| 2005/0080476 A1 | 4/2005 | Gunderson et al. |
| 2005/0090890 A1 | 4/2005 | Wu et al. |
| 2005/0149159 A1 | 7/2005 | Andreas et al. |
| 2005/0165352 A1 | 7/2005 | Henry et al. |
| 2005/0209670 A1 | 9/2005 | George et al. |
| 2005/0209672 A1 | 9/2005 | George et al. |
| 2005/0240254 A1 | 10/2005 | Austin |
| 2005/0256562 A1 | 11/2005 | Clerc et al. |
| 2005/0273151 A1 | 12/2005 | Fulkerson et al. |
| 2006/0015171 A1 | 1/2006 | Armstrong |
| 2006/0030923 A1 | 2/2006 | Gunderson |
| 2006/0074477 A1 | 4/2006 | Berthiaume et al. |
| 2006/0085057 A1 | 4/2006 | George et al. |
| 2006/0100686 A1 | 5/2006 | Bolduc et al. |
| 2006/0212105 A1 | 9/2006 | Dorn et al. |
| 2006/0259124 A1 | 11/2006 | Matsuoka et al. |
| 2006/0282152 A1 | 12/2006 | Beyerlein et al. |
| 2007/0055338 A1 | 3/2007 | Dorn |
| 2007/0055339 A1 | 3/2007 | George et al. |
| 2007/0055340 A1 | 3/2007 | Pryor |
| 2007/0055342 A1 | 3/2007 | Wu et al. |
| 2007/0060943 A1 | 3/2007 | Dorn et al. |
| 2007/0060999 A1 | 3/2007 | Randall et al. |
| 2007/0073379 A1 | 3/2007 | Chang |
| 2007/0083256 A1 | 4/2007 | Dorn |
| 2007/0100420 A1 | 5/2007 | Kavanagh et al. |
| 2007/0100422 A1 | 5/2007 | Shumer et al. |
| 2007/0118201 A1 | 5/2007 | Pappas et al. |
| 2007/0118206 A1 | 5/2007 | Colgan et al. |
| 2007/0179519 A1 | 8/2007 | Huisun |
| 2007/0191864 A1 | 8/2007 | Shumer |
| 2007/0191865 A1 | 8/2007 | Pappas |
| 2007/0191925 A1 | 8/2007 | Dorn |
| 2007/0219624 A1 | 9/2007 | Brown et al. |
| 2010/0179637 A1 | 7/2010 | Dorn et al. |

FOREIGN PATENT DOCUMENTS

| | | | |
|---|---|---|---|
| DE | 19936059 A1 | 2/2001 | |
| DE | 10201151 A1 | 7/2003 | |
| EP | 0221570 A2 | 5/1987 | |
| EP | 0380873 A2 | 8/1990 | |
| EP | 380873 A2 | 8/1990 | * |
| EP | 0380873 A2 | 8/1990 | |
| EP | 0436303 A1 | 7/1991 | |
| EP | 505686 A1 | 9/1992 | |
| EP | 0564894 A1 | 10/1993 | |
| EP | 0611556 A1 | 8/1994 | |
| EP | 611556 A1 | 8/1994 | * |
| EP | 0630657 A1 | 12/1994 | |
| EP | 0699451 A2 | 3/1996 | |
| EP | 0611556 A1 | 8/1999 | |
| EP | 941716 A2 | 9/1999 | |
| EP | 1084728 A1 | 3/2001 | |
| EP | 1095634 A2 | 5/2001 | * |
| EP | 1095634 A2 | 5/2001 | |
| EP | 1488763 A2 | 12/2004 | |
| GB | 0114939.2 | 8/2001 | |
| JP | 1150516 A | 6/1989 | |
| JP | 3725550 T | 5/1999 | |
| JP | 11505162 | 5/1999 | |
| JP | 11313893 A | 11/1999 | |
| JP | 2004530507 T | 10/2004 | |
| WO | 9636298 A1 | 11/1996 | |
| WO | 9639998 A2 | 12/1996 | |
| WO | WO 97/07756 A1 | 3/1997 | |
| WO | 9812988 A1 | 4/1998 | |
| WO | 9814224 A2 | 4/1998 | |
| WO | 9925280 A1 | 5/1999 | |
| WO | 9944541 A1 | 9/1999 | |
| WO | 9947075 A1 | 9/1999 | |
| WO | 9951167 A2 | 10/1999 | |
| WO | 0000104 A1 | 1/2000 | |
| WO | 0071059 A1 | 11/2000 | |
| WO | 0078248 A1 | 12/2000 | |
| WO | 0117458 A1 | 3/2001 | |
| WO | 0134061 A1 | 5/2001 | |
| WO | 0164134 A1 | 9/2001 | |
| WO | WO 01/64134 A1 | 9/2001 | |
| WO | 0215820 A2 | 2/2002 | |
| WO | 02087470 A1 | 11/2002 | |
| WO | 2004062458 A2 | 11/2002 | |
| WO | 02102279 A2 | 12/2002 | |
| WO | 03002019 A2 | 1/2003 | |
| WO | 03002020 A2 | 1/2003 | |
| WO | 03003944 A2 | 1/2003 | |
| WO | 2005053574 A2 | 6/2005 | |

OTHER PUBLICATIONS

Jun. 10, 2009 International Search Report in international application No. PCT/EP2007/063347 filed on Dec. 5, 2007.

Jun. 10, 2009 Written Opinion of the International Search Authority in international application No. PCT/EP2007/063347 filed on Dec. 5, 2007.

Oct. 26, 2009 Japanese Office action in Japanese patent application No. 2006-500573.

Nov. 22, 2004 International Search Report in international application No. PCT/EP2004/000248 filed on Jan. 15, 2004.

Nov. 11, 2004 Written Opinion of the ISA in international application No. PCT/EP2004/000248 filed on Jan. 15, 2004.

Jul. 15, 2005 International Preliminary Report on Patentability in international application No. PCT/EP2004/000248 filed on Jan. 15, 2004.

Jun. 23, 2009 Examiner's Requisition in Canadian application No. 2,513,082 filed on Jan. 15, 2004.

Oct. 7, 2005 International Search Report in international application No. PCT/EP2004/013339 filed on Nov. 24, 2004.

Oct. 7, 2005 Written Opinion of the ISA in international application No. PCT/EP2004/013339 filed on Nov. 24, 2004.

Apr. 1, 2007 International Preliminary Report on Patentability in international application No. PCT/EP2004/013339 filed on Nov. 24, 2004.

Jan. 24, 2003 International Search Report in international application No. PCT/EP2002/11082 filed on Oct. 2, 2002.

Jan. 7, 2004 International Preliminary Report on Patentability in international application No. PCT/EP02/11082 filed on Oct. 2, 2002.

Jan. 23, 2003 International Search Report in international application No. PCT/EP02/07435 filed on Jul. 4, 2002.
Jan. 20, 2003 International Preliminary Report on Patentability in international application No. PCT/EP02/07435 filed on Jul. 4, 2002.
Apr. 6, 2009 Advisory Action for U.S. Appl. No. 10/483,020, filed Mar. 31, 2004.
Aug. 18, 2008 Non-Final Office Action in U.S. Appl. No. 10/483,020, filed Mar. 31, 2004.
Feb. 1, 2010 Advisory Action for U.S. Appl. No. 10/580,200, filed Mar. 30, 2007.
Feb. 3, 2009 Final Office Action in U.S. patent application No. 10/483,020, filed Mar. 31, 2004.
Jan. 28, 2009 Notification of Reasons for Rejection in JP 2003-509960.
Jul. 11, 2008 Notification of Reasons for Rejection for corresponding JP 2003-509960.
Jul. 21, 2009 Non-Final Office Action in U.S. Appl. No. 10/483,020, filed Mar. 31, 2004.
Mar. 16, 2010 Final Office Action for U.S. Appl. No. 10/483,020, filed Mar. 31, 2004.
Mar. 2, 2010 Non-final Office Action for U.S. Appl. No. 10/580,200, filed Mar. 30, 2007.
Mar. 22, 2010 Non-final OA for U.S. Appl. No. 10/541,875, filed Apr. 5, 2006.
Mar. 30, 2009 Non-Final Office Action in U.S. Appl. No. 10/580,200, filed Mar. 30, 2007.
Nov. 9, 2009 Final Office Action in U.S. Appl. No. 10/580,200, filed Mar. 30, 2007.
PCT/EP2007/063347 filed on Dec. 5, 2007 Preliminary Examination mailed Jun. 10, 2009.
Sep. 14, 2009 Office Action in Japanese patent application No. 2003-509960.
U.S. Appl. No. 10/483,020, filed Mar. 31, 2004 Final Office Action dated Sep. 13, 2010.
U.S. Appl. No. 10/541,875, filed Apr. 5, 2006 Final Office Action dated Jul. 16, 2010.
U.S. Appl. No. 10/541,875, filed Apr. 5, 2006 Advisory Action dated Sep. 30, 2010.
U.S. Appl. No. 10/580,200, filed Mar. 30, 2007 Final Office Action dated Sep. 1, 2010.

* cited by examiner

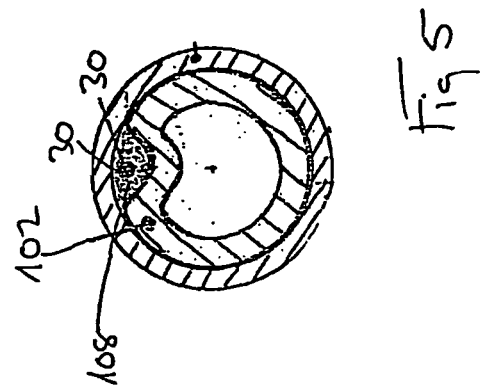
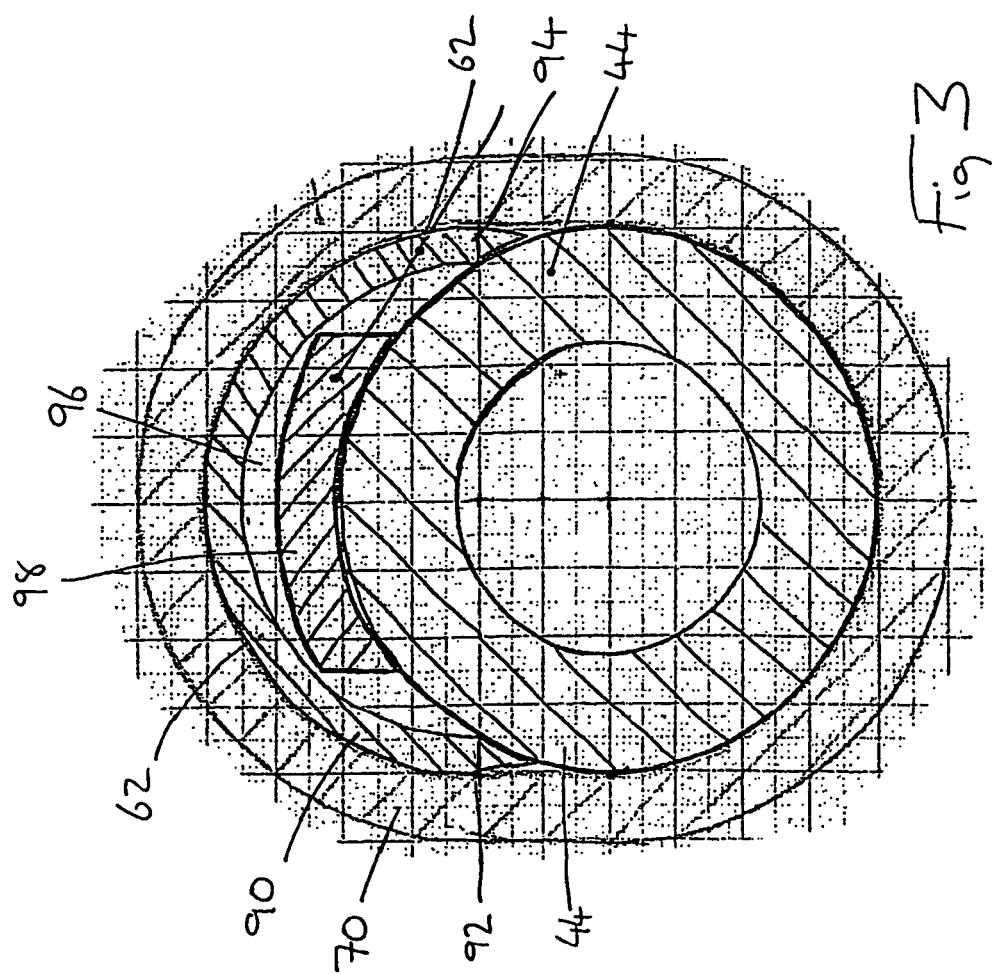

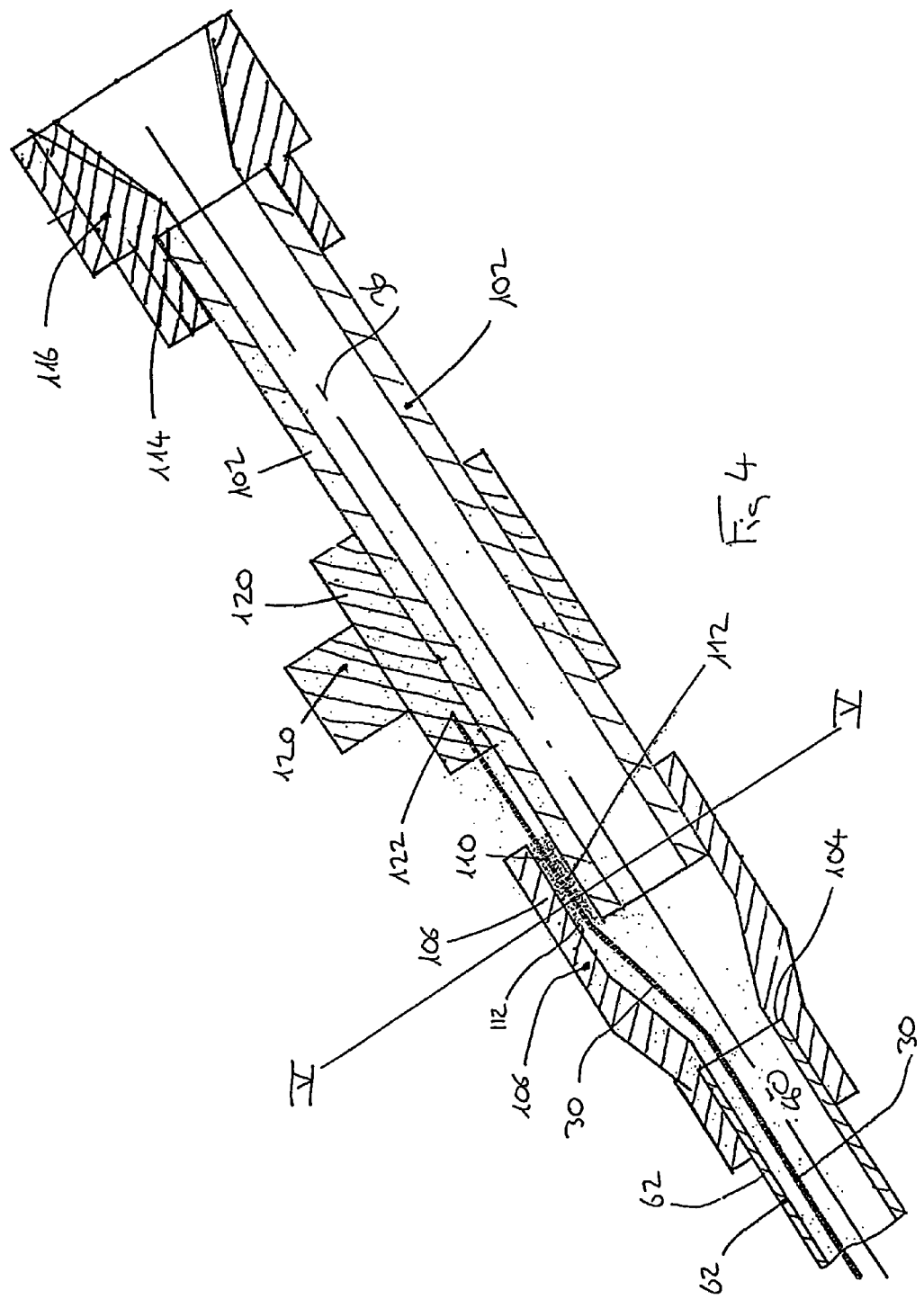

STENT DELIVERY SYSTEM

This invention relates to a stent delivery system comprising a sleeve to surround a self-expanding stent, to be retracted proximally, relative to the stent, to release the stent progressively, starting with the distal end of the stent, an abutment to engage the stent, within the volume defined by the sleeve, to restrain the stent from moving proximally, as the sleeve is retracted proximally, and a tubular lumen-defining catheter shaft extending proximally from the abutment, which resists axial compressive stresses during proximal withdrawal of the sleeve. A tension member runs the length of the catheter shaft, receives a tensile stress at its proximal end and thereby imposes on the sleeve an axial stress for said proximal retraction of the sleeve relative to the stent. The catheter shaft includes a proximal guidewire lumen exit port remote from the proximal end of the catheter shaft, whereby the stent delivery system is a rapid exchange system. The tubular shaft carries at its distal end an inner catheter, which defines a guidewire lumen and extends from a proximal end at the proximal guidewire lumen exit port to a distal end which defines a distal guidewire lumen exit port at the distal end of the sleeve. Such a rapid exchange stent delivery system is disclosed in EP-A1-0 505 686.

BACKGROUND ART

Catheter systems and stent delivery systems are similar, to the extent that each is usually deployed by advancing it along a guidewire. Not infrequently, there will be exchanges of such devices while the guidewire remains in place. Systems which are categorised as "over the wire" have a guidewire lumen which runs the full length of the device. As this is typically of the order of 130 cm, it can be cumbersome and inconvenient to exchange for a different device while the guidewire remains in place, leading to the site of surgical treatment.

By contrast, the so-called "rapid exchange" catheter systems have a guidewire lumen which runs much less than the full length of the system, and only in a distal portion of the length. In such systems, the length of guidewire protruding from the body of the patient during exchange of one catheter system for another, over the same guidewire, need be only a fraction of the full length of the catheter system, making it easier and quicker to make the exchange. This is a good reason for preferring rapid exchange systems to "over-the-wire" systems, other things being equal.

An early example of a rapid exchange catheter system is to be found in EP-A-0 380 873. The system shows a balloon catheter with a substantial part of its length defined by a hypotube which delivers inflation fluid to a balloon at the distal end of the catheter. Running through the balloon is a tube defining a guidewire lumen extending from a distal exit port distal of the balloon to a proximal guidewire exit port some distance proximal of the balloon. Proximal of the proximal guidewire port, the guidewire runs parallel to the hypotube shaft, but outside it. Advancing the catheter device over the guidewire is relatively simple, because the guidewire lumen is more or less straight, with a continuous smooth luminal wall surface.

Reference is now made to the stent delivery system disclosed in EP 505 686. It is to be noticed that the path of the guidewire through the stent delivery system of EP 505 686 is significantly more complicated than that of EP 380 873. Not only does the guidewire pass through the cylindrical wall of the catheter body on which the balloon is mounted, but also through the cylindrical wall of a sheath element which surrounds the stent and which is retracted, relative to the catheter body, for deployment of the stent. To accommodate the guidewire during stent deployment, the sheath 10 has not only a proximal guidewire exit port but also a long slit, the walls of which slide over the guidewire during proximal retraction of the sheath. Furthermore, to deflect the guidewire out of the proximal exit port in the cylindrical wall of the catheter body, there is provided a plug with a tapered end surface which will guide the proximal end of the guidewire, during backloading of the catheter device onto the guidewire, out of the lumen of the catheter body, through the proximal guidewire exit port.

SUMMARY OF THE INVENTION

It is an object of the present invention to simplify the construction of rapid exchange stent delivery systems, in particular in the area of the guidewire lumen.

According to one embodiment of the present invention, there is provided a stent delivery system as specified in the opening paragraph of this description, which is characterised in that the inner catheter and the tubular shaft are arranged parallel between the distal end of the catheter shaft and the proximal guidewire exit port with spacing therebetween to accommodate the tension member at a location outside the guidewire lumen yet inside the lumen of the catheter shaft.

By providing a gap for the tension member, between the tube which defines the guidewire lumen, and the tube which defines the catheter shaft, one can provide an uncluttered path for the guidewire and a straight path for the tension member, together in a catheter system which displays a notably smooth outer cylindrical surface throughout its length.

Furthermore, by providing a system for delivery of a self-expanding stent which exhibits, over a very large part of its length, both a metallic catheter shaft to be put in compression during deployment of the stent, and a metallic tension member to pull the sleeve proximally off the abluminal surface of the stent, one avoids the adverse effects of time-dependent strain which polymers exhibit when put under stress. Such time-progressive strain can complicate the task of placing a self-expanding stent, under radioscopic observation, at precisely the desired position axially along the length of the bodily lumen being stented.

Thus, an advantageous construction for stent delivery systems in accordance with this invention is a catheter shaft formed of a metallic tube, in combination with a tension member which is a metallic wire. Conveniently, the tension member is fixed to the sleeve which is to surround the stent, by a connection ring, coaxial with the sleeve, and fixed to the sleeve. The connection ring is advantageously of metal. This would allow it to serve as a radiopaque marker for the stent. In any case, it enables a reliable metal-to-metal connection with the tension member. It may be advantageous to provide a pair of coaxial connection rings, one inside and one outside the sleeve. The sleeve would normally be formed from a synthetic polymer, possibly a construction incorporating braiding reinforcement, and advantageously with a taper at its distal tip. Furthermore, it may be convenient and advantageous to provide on the sleeve, just proximal of the distal tip zone, a radiopaque marker for the distal end of the stent.

In a construction in which the sleeve incorporates braiding, the connection ring could incorporate radially-extending bosses or other protuberances, to extend into or through interstices in the braiding, thereby enhancing the security of the sleeve-ring bond when the assembly is in axial tension.

The guidewire lumen is provided by an inner catheter, cantilevered from the distal end of the catheter shaft. Conveniently, the distal end of the catheter shaft is cut away to provide a lengthwise slot, with a length direction parallel to the axis of the catheter shaft, and open-ended at its distal end, coinciding with the distal end of the catheter shaft. In one preferred embodiment, the tube which defines the guidewire lumen is set inside the lumen of the catheter shaft, with the proximal end of the inner catheter debouching at the proximal end of the open-ended slot, to define the proximal guidewire lumen exit port, on the cylindrical surface of the catheter shaft, at the proximal end of the lengthwise slot.

Advantageously, the inner catheter sits within the lumen of the catheter shaft, along the length of its lengthwise slot, with spacing between the abluminal surface of the inner catheter and the luminal surface of the catheter shaft opposite the lengthwise slot, thereby affording a crescent-shaped lumen, within the catheter shaft but outside the inner catheter, for the tension member to pass from the lumen of the catheter shaft proximal of the lengthwise slot, to positions distally beyond the distal end of the catheter shaft.

Advantageously, a catheter shaft extension tube is provided, with a diameter large enough to extend around the catheter shaft and inner catheter over the full length of the lengthwise slot in the catheter shaft. In this way, the catheter shaft extension tube can bind together, over the length of the lengthwise slot, the catheter shaft and the inner catheter. Furthermore, the catheter shaft extension can maintain a continuous fluid lumen between the lumen of the catheter shaft, in which the tension member is housed, and the lumen of the sleeve to surround the stent. In this way, flushing fluid can be introduced into the catheter shaft lumen at the proximal end of the catheter shaft and can advance the full length of the catheter shaft, through the crescent lumen where the lengthwise slot is located, into the lumen of the catheter shaft extension, and onwards distally into the lumen of the sleeve, thereby serving to flush any gas from all of the luminal volume of the catheter system except the lumen of the guidewire. It will be appreciated that, during deployment of the stent by proximal withdrawal of the sleeve, the sleeve will advance proximally over the abluminal surface of the catheter shaft extension.

The inner catheter extends distally through the lumen of the stent. If the stent is not to travel proximally with the surrounding sleeve, when the sleeve is withdrawn proximally, then the inner catheter should carry an abutment which engages the stent and restrains the stent from moving proximally. This is conveniently provided by an annulus of synthetic polymeric material, mounted on the abluminal surface of the inner catheter, just proximal of the axial location of the stent and with a distal-facing abutment surface to contact the stent. Conveniently, this annulus of polymer can include a metallic ring to serve as a radiopaque marker for the proximal end of the stent. However, in embodiments where the abutment is within the stent length, it may be effective to use the above-mentioned connection ring as a proximal radiopaque stent marker.

If desired, the stent abutment can be shaped so as to afford a fluid passage between the annulus and the surrounding sleeve, to enable flushing of the annular volume of the delivery system, distal of the abutment annulus.

Turning to the proximal end of the delivery system, it can readily be arranged for the tension member to exit the lumen of the catheter shaft at the junction of the proximal end of the catheter shaft and the distal end of a shaft continuation, through a packing which is an adequate seal against outflow of flushing fluid. Then, flushing fluid can be introduced at the proximal end of the shaft continuation and can flow distally through the length of the shaft continuation, past the exit point of the tension member, and into the proximal end of the catheter shaft. Readers will be well-aware how to provide a suitable flushing port at the proximal end of the shaft continuation.

Advantageously, one may mount on the cylindrical outside surface of the shaft continuation a retraction handle which grips the proximal end of the tension member, whereby translation proximally of the retraction handle along the length of the shaft continuation achieves the desired tension in the tension member, proximal movement of the tension member, and consequent proximal movement of the sheath surrounding the stent.

For a better understanding of the present invention, and to show more clearly how the same may be carried into effect, reference will now be made, by way of example, to the accompanying drawings, in which:

FIG. 3 is a transverse section through the line of FIG. 2;

FIG. 4 is a longitudinal diametral section of the proximal end of the system of FIG. 1.

FIG. 5 is a transverse section along the VV of FIG. 4.

Figure 1:
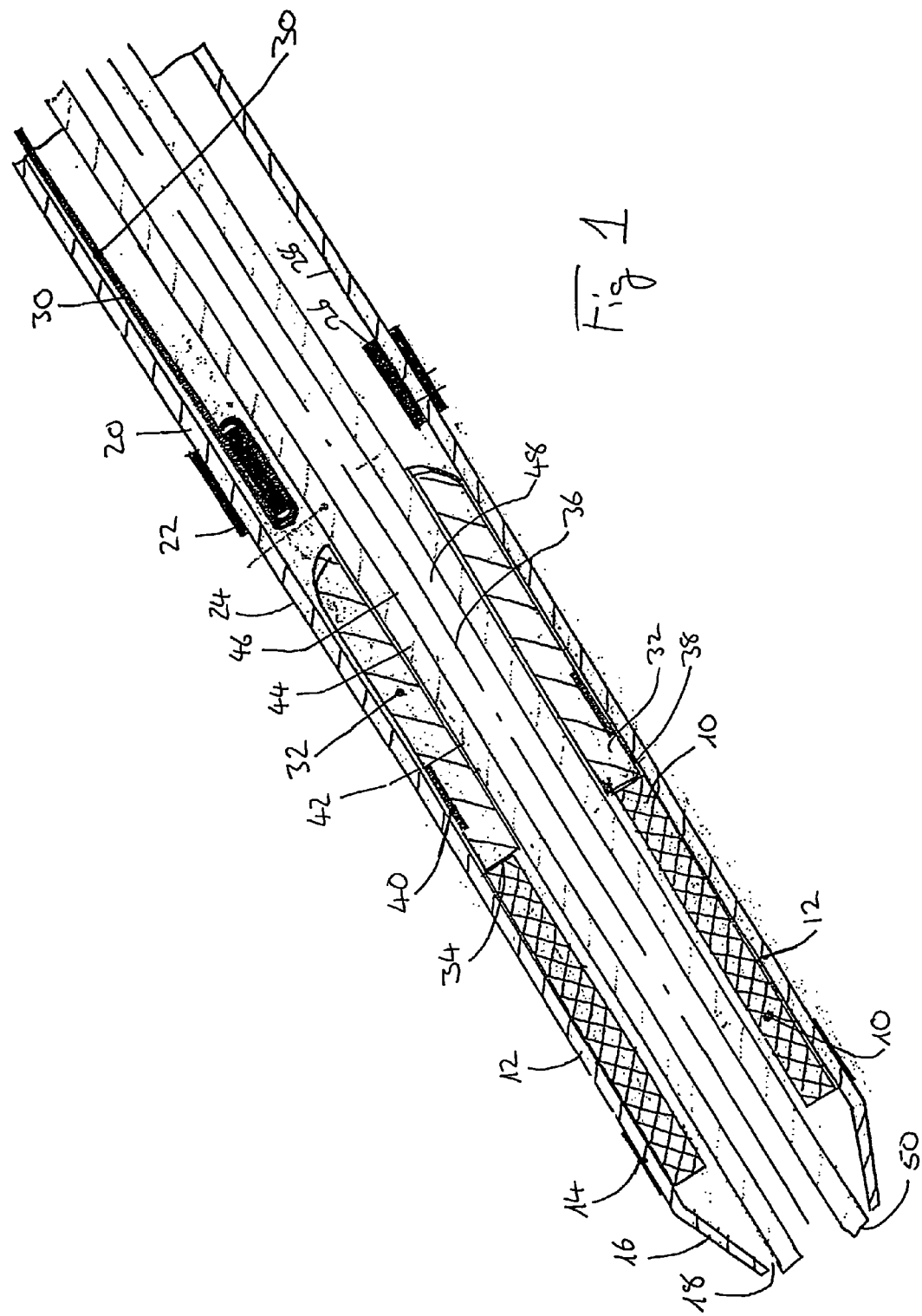
FIG. 1 is a longitudinal diametral section of the distal end of the stent delivery system.

Referring to drawing FIG. 1, a stent 10 which is a self-expanding stent such a nickel titanium shape memory alloy stent made and sold by the present applicant under the trademark Memotherm™, is constrained to a relatively small diameter by a surrounding sheath 12. The sheath 12 carries a metal band 14 near its distal tip, which constitutes a radiopaque marker band to indicate the location of the distal end of the stent 10. The sleeve 12 extends distally into a tapered tip 16 which terminates in a distal axial opening 18. Proximal of the stent 10, the sheath extends further proximally, to a connection zone 20 within which is found a pair of connection rings, coaxially arranged, with the larger ring 22 on the abluminal surface 24 of the sheath, and the smaller ring 26 in contact with the luminal surface 28 of the sheath 12. The bulk thickness of the material of the wall of the sheath 12 is compressed radially between the two coaxial connection rings. Bonded to the inner ring 26 is a tension wire 30 which extends the full length of the shaft of the stent delivery system. Conveniently, the inner ring 26 and the tensile wire 30 are of metal so can readily and reliably be bonded together by a procedure such as brazing. It is tension imposed on the tension wire 30 which will, in deployment of the stent 10, pull the sheath 12 proximally, relative to the stent 10, to release the stent progressively, from its distal end to its proximal end.

However, proximal movement of the sheath 12 relative to the stent 10 is possible only if the stent 10 is constrained from being carried proximally with the sheath 12. The task of restraining the stent 10 from moving proximally is carried by an abutment element 32 which is in the form of a collar of synthetic polymer having a distal end surface 34 which is transverse to the long axis 36 of the system and which contacts the proximal end surface 38 of the stent 10. The abutment collar 32 carries a metallic ring 40 on its radially outer surface, this metal ring serving as a radiopaque marker to indicate the location of the proximal end of the stent 10.

Figure 2:
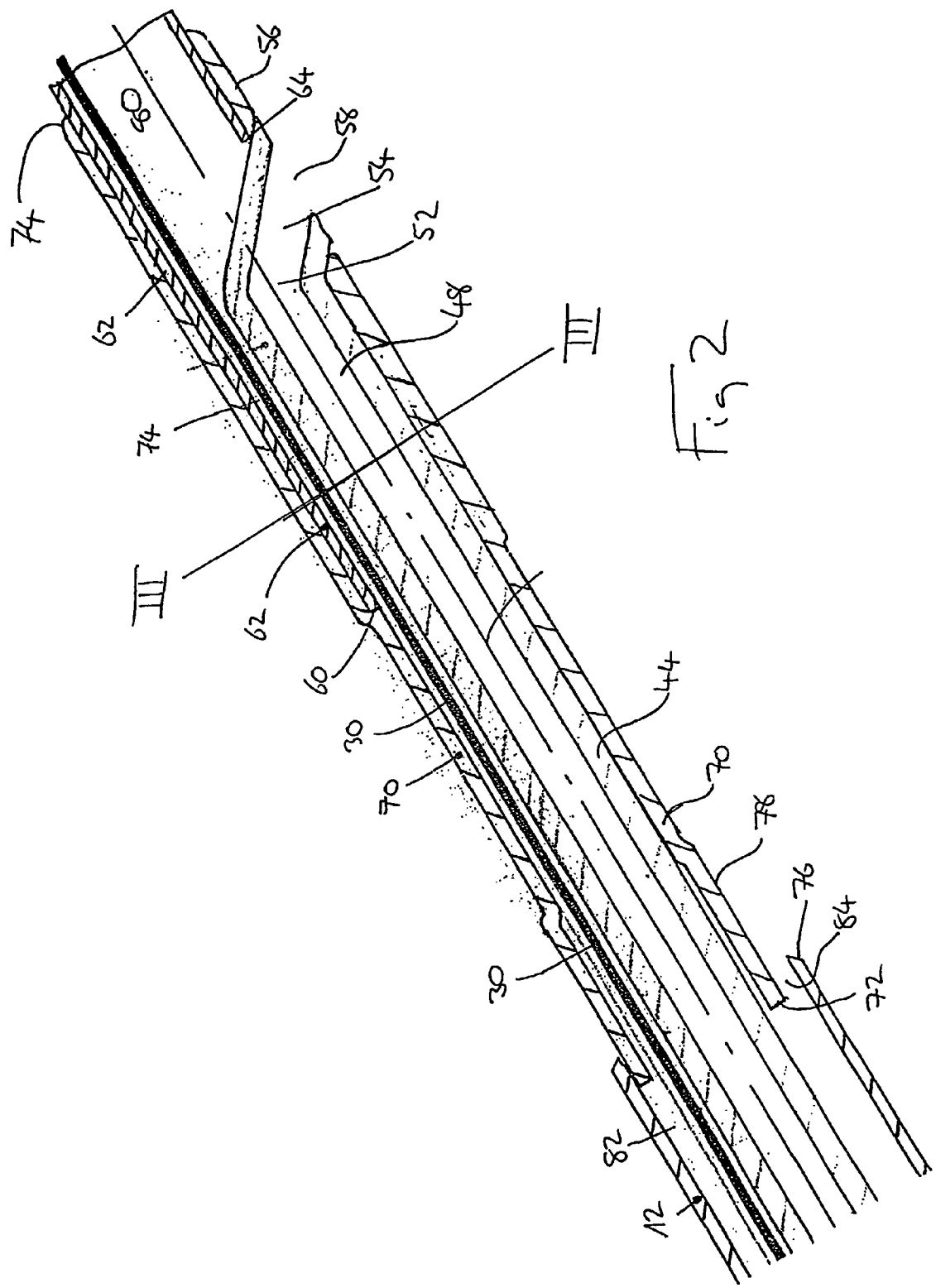
FIG. 2 is longitudinal diametral section of part of the length of the system of claim 1, including the proximal guidewire lumen exit port.

The abutment collar 32 is itself mounted fixedly on the cylindrical abluminal surface 42 of an inner catheter 44 which defines a lumen wall 46 of a guidewire lumen 48. The inner catheter 44 extends distally to a distal end 50 just distal of the distal end opening 18 of the sheath 12. The inner catheter 44 is of synthetic polymeric material but is resistant to end-wise compression. It extends proximally a significant distance beyond the connection rings 22, 26. Reference is now made to FIG. 2, for a description of the proximal portions of the inner catheter 44.

In FIG. 2, the inner catheter 44 is seen to extend proximally as far as an elbow 52 where the guidewire lumen 48 turns off the long axis 36 of the device and follows a path 54 with its length direction inclined at about 60 degrees to the axis 36, for a short distance until it reaches the cylindrical surface 56 of the system and there defines a proximal guidewire lumen exit port 58. This exit port 58 is proximal of the distal end 60 of a stainless steel hypotube catheter shaft element 62 of the system. This tube 62 has a distal end zone extending between the distal end 60 of the tube and the proximal end 64 of a lengthwise slit (described below with reference to FIG. 3) in the cylindrical wall of the hypotube 62. The proximal end 64 of the slit coincides with the proximal end of the guidewire exit port 58.

Surrounding the distal end zone of the hypotube 62 is a tube 70 of synthetic polymeric material which constitutes a catheter shaft extension cantilevered distally beyond the distal end 60 of the tube 62. This shaft extension has a distal end 72 and a proximal end 74 which lies proximal of the proximal end 64 of the guidewire exit port 58. A hole is formed in the cylindrical wall of the tube 70, to coincide with the guidewire exit port 58. It will be appreciated that luminal surface area of the tube 70, in the axial length between the distal end 60 of the tube 62 and the proximal end 64 of the guidewire exit port 58 contacts both the abluminal wall of the catheter shaft tube 62 and the abluminal wall of the inner catheter 44. Indeed, the tube 70 serves to sleeve both of the elements simultaneously, and to bond them together and hold them in fixed axial relationship, one with the other.

As can be seen in FIG. 2, there is a passage for the tension wire 30 between the luminal surface of the hypotube 62 and the abluminal surface of the inner catheter 44, in the zone between the guidewire exit port 58 and the distal end 60 of the tube 62. For further information about the shape of this tension wire lumen 74, please refer to FIG. 3 and the corresponding description below. As can be seen in FIG. 2, the tension wire 30 continues proximally, through the part of the axial length of the delivery system shown in FIG. 2, towards the proximal end of the system, without needing significantly to deviate from a straight path.

As also can be seen from FIG. 2, the proximal end 76 of the outer sheath 12 is located proximal of the distal end 72 of the shaft extension tube 70 so that, on imposing an adequate tension on the tension wire 30 to withdraw the outer sheath 12 proximally, the luminal surface 28 of the outer sheath 12 can pass along the abluminal surface 78 of the extension tube 70. While considering FIG. 2, note that flushing fluid advancing distally along the lumen 80 of the catheter shaft tube 62 can continue to advance distally along the rather smaller cross-section lumen 74 and, from there, into the lumen 82 defined by the outer sheath 12. Depending how snug is the fit between the outer sheath 12 and the shaft extension tube 70, flushing fluid may or may not exit the system through the annulus 84 between the sleeve 12 and tube 70. Otherwise, the flushing fluid can advance further distally, through the zone of length shown in FIG. 1 until eventually exiting the system through the annulus between the inner catheter 44 and the distal end opening 18 of the sheath 12.

Moving on to FIG. 3, here we see the shaft extension tube 70 sleeving an arc 90 of the shaft tube 62. The lengthwise slot of the shaft tube 62 corresponds to the missing part of the circular circumference absent from FIG. 3. In FIG. 3, the circumferential arc 90 of the tube 62, extending over somewhat more than a half circle, defines a trough with spaced parallel lips 92, 94, to receive between its wings the inner catheter element 44. Sleeving both the inner catheter 44 and the circumferential arc 92 of the catheter shaft tube 62 is the polymeric annulus of the shaft extension 70. Between the luminal surface of the arc 90 and the outside cylindrical surface of the inner catheter tube 44 is defined a crescent-shaped lumen 96 within which the tension wire 98 can be seen. Preferably, the cross-sectional shape of the tension wire 98 is chosen to take best advantage of the special shape of the lumen 96 in which it slides. It will be evident from FIG. 3 that the sleeving member 70 affords ample opportunity to achieve a secure bond between the respective components of the system so as to minimise the possibility for any axial movement of the inner catheter 44 relative to the catheter shaft 62.

Turning now to FIG. 4, there is shown the proximal end of the catheter shaft 62 and tension wire 30. By providing a shaft continuation tube 102, collinear but spaced from the proximal end 104 of the shaft 62, and fixed thereby a flared connector element 106, there is an opportunity to lead the tension wire 30 out of the lumen 80 of the catheter shaft. Indeed, as can be seen in FIG. 5, the wall of the shaft continuation 102 can be deformed inwardly to create a lengthwise groove 108 on the abluminal surface of the continuation tube 102, to afford an exit route 110 for the tension wire 30 between the luminal surface of the connector element 106 and the abluminal surface of the shaft continuation 102. This groove can be packed with a sealing material 112.

At the proximal end 114 of the shaft continuation 102 is a flushing port annulus 116, the construction of which will be familiar to those skilled in this art.

On the cylindrical outer surface of the shaft continuation 102 can be slidably mounted a retraction handle, otherwise called slider, 120. As shown, the proximal end 122 of the tension wire 30 is fixedly mounted to the slider 120. It will be evident that proximal withdrawal of the sheath 12 from the stent 10 is accomplished by a controlled proximal movement of the slider 120 approximately along the long axis 36 of the device, sliding along the abluminal surface of the shaft continuation 102.

In use, the stent delivery system can be back loaded onto an in situ guidewire, by introducing the proximal end of the guidewire into the distal end 50 of the inner catheter 44, and advancing the stent delivery system distally along the guidewire until the proximal end of the guidewire emerges from the proximal guidewire exit port 58. After that, the distal end of the stent delivery system can be advanced distally further along the guidewire, until the stent is in position for stent release. Once the desired stent position is achieved and confirmed, stent release may follow, by moving the slider 120 proximally. The sheath 12 moves proximally, the stent is released, and then the delivery system can be withdrawn proximally over the guidewire.

The embodiment shown in the drawings and described above is but one way to realise the subject matter of this invention. Those skilled in the art will be able to realise the invention in different embodiments. It is the claims which follow which are intended to indicate the scope of protection sought by this patent application.

The invention claimed is:

1. A stent delivery system comprising:
   i) a sleeve to surround a self-expanding stent, to be retracted proximally, relative to the stent, to release the stent progressively, starting with a distal end of the stent;
   ii) an abutment to engage the stent, within the volume defined by the sleeve, to restrain the stent from moving proximally, as the sleeve is retracted proximally;

iii) a tubular, lumen-defining catheter shaft extending proximally from the abutment, which resists axial compressive stresses during proximal withdrawal of the sleeve;
iv) a tension member which runs a length of the catheter shaft, which receives a tensile stress at a proximal end of the tension member and thereby imposes on the sleeve an axial stress for said proximal retraction of the sleeve relative to the stent, the tension member connecting to a connection ring inside the sleeve and coaxially arranged with a larger ring on an abluminal surface of the sleeve opposite the connection ring;
v) the catheter shaft includes a proximal guidewire lumen exit port remote from a proximal end of the catheter shaft, whereby the stent delivery system is a rapid exchange system; and
vi) the catheter shaft carries at a catheter shaft distal end an inner catheter, which defines a guidewire lumen and extends from an inner catheter proximal end at the proximal guidewire lumen exit port to an inner catheter distal end which defines a distal guidewire lumen exit port at a distal end of the sleeve,
wherein the inner catheter and the catheter shaft are arranged parallel between the distal end of the catheter shaft and the proximal guidewire lumen exit port with spacing therebetween to accommodate the tension member outside the guidewire lumen and inside the lumen of the catheter shaft, a catheter shaft extension at the catheter shaft distal end, a luminal surface of the sleeve moves, during said proximal retraction, over an abluminal surface of the catheter shaft extension.

2. The system as claimed in claim 1, wherein the catheter shaft is metallic.

3. The system as claimed in claim 1 or 2, wherein the tension member is a wire.

4. The system as claimed in claim 1, wherein the sleeve carries a marker band to indicate the distal end of the stent.

5. The system as claimed in claim 1, including at the proximal end of the catheter shaft a shaft continuation and a proximal exit port for the tension member, between the catheter shaft and the shaft continuation.

6. The system as claimed in claim 5, wherein the shaft continuation has at its proximal end a port for flushing the catheter shaft.

7. The system as claimed in claim 6, wherein the shaft continuation carries a slider to which the proximal end of the tension member is connected, whereby proximal movement of the slider on the shaft continuation retracts the sleeve proximally relative to the catheter shaft.

8. The system as claimed in claim 1, wherein the distal end of the catheter shaft defines a lengthwise slot open-ended at its distal end, thereby to define a trough which through the inner catheter is received, the proximal guidewire lumen exit port being coincident with the proximal end of the slot and trough.

9. The system as claimed in claim 8, wherein the outer surface of the inner catheter is spaced from a part of a surface of the trough which is circumferentially opposite from the lengthwise slot, thereby affording a lumen between the catheter shaft and the inner catheter along which the tension member extends.

10. The system as claimed in claim 8 or 9, wherein the distal end of the catheter shaft, and the inner catheter lying in its trough, are sleeved by the catheter shaft extension which extends as a cantilever from the distal end of the catheter shaft.

11. The system as claimed in claim 10, wherein the catheter shaft extension has a distal end which is received within a proximal end opening of the sleeve.

12. The system as claimed in claim 1, wherein the sleeve has a distal end which tapers inwardly.

13. The system as claimed in claim 1, wherein the abutment comprises a radiopaque marker.

14. The system as claimed in claim 1, the luminal surface of the sleeve and the abluminal surface of the catheter shaft extension defining an annulus therebetween permitting passage of a fluid through the annulus.

15. The system as claimed in claim 1, the outer surface of the inner catheter and an inner surface of the catheter shaft extension defining a space therebetween occupied in part by the tension member, the stent delivery system defining a common longitudinal axis of the catheter shaft, the inner catheter, and the sleeve, the longitudinal center of the catheter shaft extension offset from the common longitudinal axis by a radial distance of the space.

16. The device of claim 1, the tension member having an arcuate cross section.

17. A stent delivery device, comprising:
a catheter shaft having proximal and distal ends and defining a lumen extending between the proximal and distal ends;
a catheter shaft extension disposed on the distal end of the catheter shaft and extending distally, the catheter shaft extension defining a first central axis and a lumen communicating with the lumen of the catheter shaft, a wall of the catheter shaft extension defining a proximal guidewire port;
a guidewire shaft defining a second central axis and disposed at the distal end of the catheter shaft and within the lumen of the catheter shaft extension, a proximal end of the guidewire shaft engaging the wall of the catheter shaft extension defining the proximal guidewire port, a distal end of the guidewire shaft extending distally, an exterior surface of the guidewire shaft and an interior surface of the catheter shaft extension defining a space therebetween;
a sheath slidably disposed around a distal end of the catheter shaft extension and extending distally to cover a stent disposed on the distal end of the guidewire shaft; and
a tension member disposed in the space, a distal end of the tension member connecting to a connecting ring inside an interior of the sheath and coaxially arranged with a larger ring on the abluminal surface of the sheath opposite the connection ring, a proximal end of the tension member disposed proximate the proximal end of the catheter shaft, wherein the first and second central axes are offset.

18. The device of claim 17, the sheath having a distal end that tapers inwardly distal to the stent.

19. The device of claim 17, a luminal surface of the sheath and the abluminal surface of the catheter shaft extension defining an annulus therebetween permitting passage of a fluid through the annulus.

20. The device of claim 17, the tension member having an arcuate cross section.

* * * * *